United States Patent [19]

Raghavachari et al.

[11] 4,048,997
[45] Sept. 20, 1977

[54] SYRINGE WITH ACTINIC RADIATION PROTECTION

[75] Inventors: Srinivas T. Raghavachari, Chicago; Robert L. Striebel, II, Evanston, both of Ill.

[73] Assignee: MPL, Inc., Chicago, Ill.

[21] Appl. No.: 737,209

[22] Filed: Nov. 1, 1976

[51] Int. Cl.² .............................................. A61M 5/00
[52] U.S. Cl. ...................................... 128/215; 128/1.1
[58] Field of Search ............ 128/215, 1.1, 2 A, 218 R, 128/218 D, 224; 250/505, 506, 510, 515, 519, 520; 350/311

[56] References Cited

U.S. PATENT DOCUMENTS

| | | | |
|---|---|---|---|
| 3,814,941 | 6/1974 | Czaplinski | 128/1.1 X |
| 3,820,541 | 6/1974 | Langan | 128/215 |
| 4,014,331 | 3/1977 | Head | 128/224 |

Primary Examiner—John D. Yasko
Attorney, Agent, or Firm—Kinzer, Plyer, Dorn & McEachran

[57] ABSTRACT

A syringe-type dispenser for medication and like applications, comprising a housing with a piston and an outlet seal at its opposite ends, containing a liquid medication or other liquid subject to deterioration from exposure to actinic light; the syringe housing is clear and transparent (preferably clear glass) but is covered with a thin resin film which inhibits the transmission of actinic light while passing other light in the visible spectrum. At least part of the protective film is readily removable to afford improved inspection of the syringe contents at the time of dispensation.

7 Claims, 4 Drawing Figures

U.S. Patent  Sept. 20, 1977  4,048,997
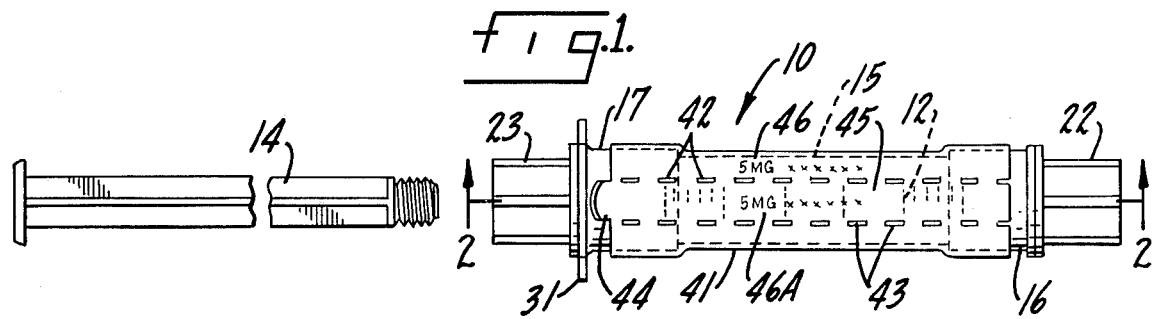
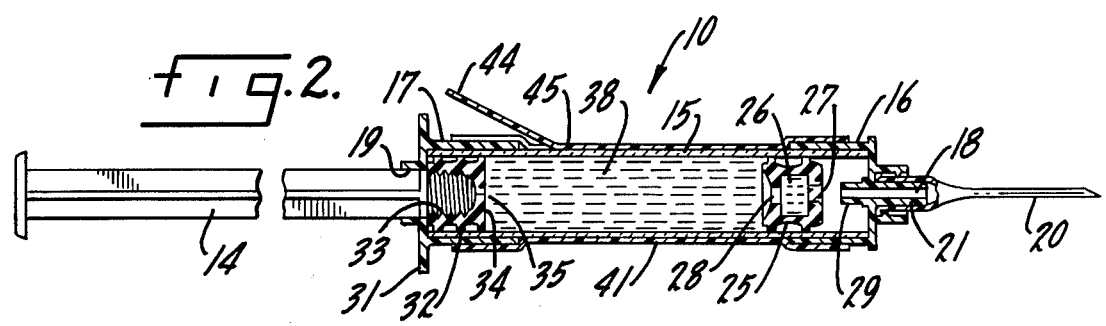
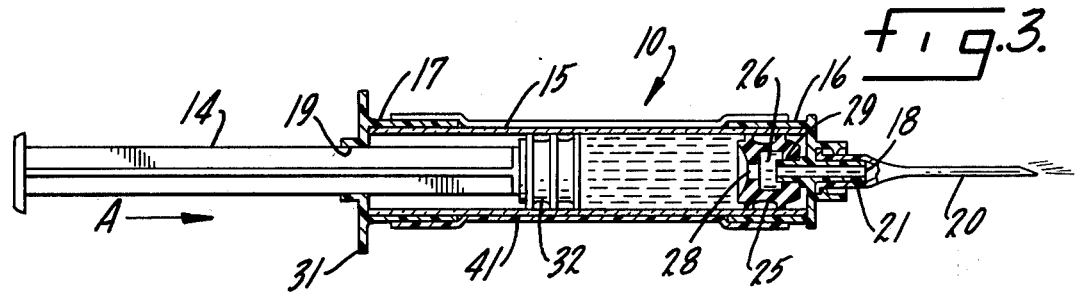
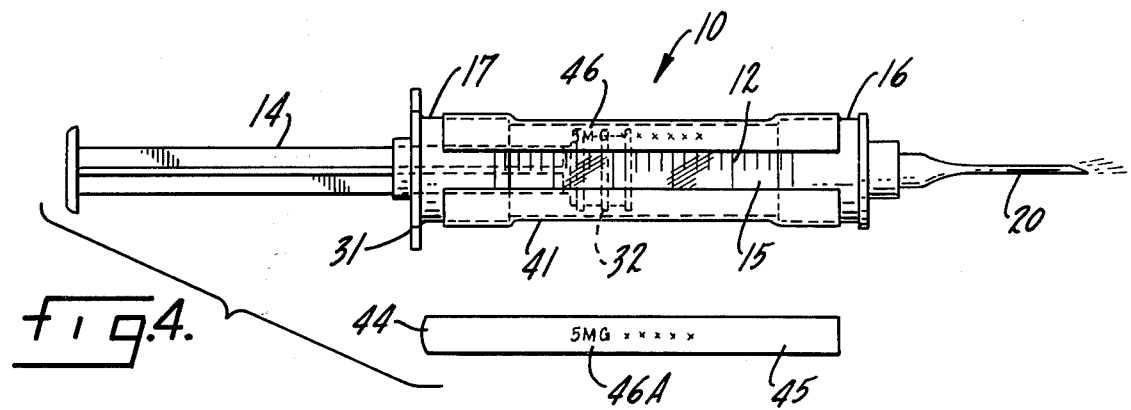

4,048,997

SYRINGE WITH ACTINIC RADIATION PROTECTION

BACKGROUND OF THE INVENTION

There are a variety of medications and other liquids that are subject to chemical change, loss of potency, or other adverse effects as the result of exposure to actinic radiation, the actinic radiation usually including light near or within the ultraviolet portion of the spectrum. Examples of medications of this kind include B complex vitamins and Dopamine. Some of these medications should not be packaged in plastic containers because they tend to absorb or react with some of the plasticizers or other constituent materials from such containers, with resultant adulteration or other deterioration.

In the field, it is often desirable to have medications pre-packaged in single-use syringes and like dispensers, including dispensers used to inject medications or other therapeutic agents into nebulizers. For medications which are subject to deterioration or degradation by exposure to actinic light, it has been customary to utilize dispenser housings formed of amber glass or other tinted glass that blocks the actinic radiation but still allows some visual inspection of the contents of the dispenser. Amber-colored or other tinted plastic housings having similar characteristics have also been employed for medications that are not subject to deterioration from contact with plastic.

The conventional practice, however, adds materially to the cost of the syringe or other dispenser, and also presents appreciable operating difficulties. Thus, the cost of amber glass tubing for a syringe housing is frequently three to four times the cost of otherwise similar tubing formed of clear, transparent glass. The cost differential per syringe is quite small, but the total cost to an institution, such as a large hospital, that may use hundreds or thousands of single-use syringes each month, can be appreciable. The inspection characteristics of amber glass or plastic syringes of this kind are rather poor; if the liquid being dispensed is relatively transparent, it may be quite difficult to determine whether the chamber within the syringe is completely full, as it must be for adequate control of administered dosage. The amber or other coloring for the syringe housing also makes it difficult to determine whether the syringe has been used previously and then perhaps refilled in whole or in part with some dilutent (e.g. water). Moreover, the amber background afforded by conventional syringes that provide protection against actinic light is a poor one for labelling purposes, which may be critical when the syringes are employed for storing and dispensing a variety of different medications.

SUMMARY OF THE INVENTION

It is a principal object of the present invention, therefore, to provide a new and improved syringe-type dispenser that affords effective protection against actinic radiation but inherently minimizes or eliminates the problems and difficulties of prior art techniques as noted above.

Another object of the invention is to provide a new and improved syringe-type dispenser which protects the contents of the dispenser against actinic light but allows for convenient and thorough visual inspection of the dispenser contents prior to use.

A further object of the invention is to provide a new and improved syringe-type dispenser that incorporates effective protection against actinic radiation and also affords a readily usable background suitable for labelling purposes.

Accordingly, the invention relates to a syringe-type dispenser for storing and dispensing a liquid which is adversely affected by exposure to actinic light, comprising a housing including a clear, transparent tube having an outlet at one end, outlet seal means, at the outlet end of the housing, including means for opening an outlet passage through the housing outlet, and a piston in the other end of the tube. The outlet seal means and the piston conjointly define a normally sealed chamber, within the tube, for storing the liquid to be dispensed, the piston being axially movable through the tube toward the outlet end of the housing to discharge the liquid through the outlet. The dispenser further comprises a thin, protective film sheath, covering and tightly fitting over the outside of the housing throughout the length of the tube between the seal means and the piston, the protective film sheath being formed of a material which inhibits the transmission of actinic light but passes other light in the visible spectrum to permit limited inspection of the dispenser contents. In the preferred construction, the protective film sheath is a length of thin thermoplastic tubing mounted on the housing in a heat-shrink high-friction fit, and is provided with means for removal of at least a part of the film from the dispenser housing to facilitate visual inspection of the syringe contents prior to use.

BRIEF DESCRIPTION OF THE DRAWINGS

FIG. 1 is an elevation view of a syringe dispenser constructed in accordance with one embodiment of the present invention;

FIG. 2 is a longitudinal section view of the dispenser taken approximately along line 2—2 in FIG. 1, with a hypodermic needle mounted on the syringe;

FIG. 3 is a sectional view, like FIG. 2, which illustrates the syringe dispenser in the course of administration of the medication; and FIG. 4 is an elevation view corresponding to FIG. 3.

DESCRIPTION OF THE PREFERRED EMBODIMENT

FIGS. 1-4 illustrate a syringe-type dispenser 10 constructed in accordance with one embodiment of the present invention. Dispenser 10 includes a plunger rod 14 that is shown detached from the remainder of the syringe in FIG. 1, as would normally be the case for shipment or storage of the dispenser.

Dispenser 10 comprises a housing including a tubular barrel 15 of clear, transparent glass, a molded resin outlet end fitting 16, and a molded resin inlet end fitting 17. Barrel 15 may be printed with a scale 12 (FIGS. 1 and 4), and other identification data. The two fittings 16 and 17 are expansion-fitted onto tube 15, affording a liquid-tight and vapor-tight housing except for an outlet 18 and an inlet 19 (FIGS. 2 and 3). In the illustrated construction, outlet 18 of syringe 11 extends through a Luer tip 21 that is formed integrally with fitting 16 and that serves as a mount for a hypodermic needle 20. However, the outlet tip 21 for syringe 10 may have a configuration for fitting into the inlet of a nebulizer, if syringe 10 is to be used as a nebulizer injector. Further, top 21 may have a nipple configuration if dispenser 10 is to be used for oral administration. In this specification, the term "syringe-type dispenser" is intended to include devices for use an hypodermic syringes, oral administration syringes, nebulizer injectors, and any other similar uses. Prior to use, as shown in FIG. 1, the tip 21 of syringe 10 is preferably covered by a molded resin cap 22. A similar cap 23 covers the inlet end of the syringe prior to use.

A valve-seal member 25 is mounted within tube 15 of syringe 10 near its outlet 18 (FIGS. 2 and 3). Valve-seal member 25 is of molded rubber or other suitable elastomer material and is of hollow construction, having a central cavity 26. The forward wall of member 25 includes a displaceable plug 27 (FIG. 2) that normally affords a liquid-tight seal, sealing the outlet end of the housing of syringe 10. An opening 28 in the rear wall of member 25 provides communication with the interior of the tubular barrel 15. A post 29 (FIGS. 2 and 3) formed integrally with fitting 16 projects rearwardly of the housing, in alignment with plug 27.

A finger-engagement flange 31 is formed integrally with fitting 17 at the inlet end of syringe 10. A piston member 32 is mounted in tube 15 at the inlet end of the syringe housing, within the portion of barrel 15 encompassed by fitting 17. Member 32 is also of molded rubber or other suitable elastomer material and has a threaded recess 33 facing the inlet opening 19 of the syringe. The inner wall 34 of member 32 comprises a slit valve 35 that is actuatable from its normal closed condition, as illustrated in FIG. 2, to an open condition (not shown), by insertion of a fill needle through the valve slit 35. Seal member 25 and piston 32, in conjunction with tube 15, define a normally sealed chamber 38 (FIG. 2) containing the medication or other liquid to be stored in and dispensed from syringe 10.

Dispenser 10, as thus far described, is a syringe of the kind manufactured and sold in substantial quantities by MPL, Inc., under the trademark SOLOPAK, for use as hypodermic syringes, oral application syringes, or nebulizer injectors. The basic syringe construction is shown in U.S. Pats. Nos. 3,803,700, 3,729,031, 3,729,032, 3,885,297, and 3,889,351. The component parts may be identical with those employed in the current commercial syringes. In the dispensers intended for oral application, as produced commercially, the combination valve and seal member 25 is not utilized, the outlet seal for the dispenser being afforded by a cap such as cap 22.

In accordance with the present invention, dispenser 10 incorporates a thin protective film sheath 41 which covers and fits tightly over the outside of the syringe housing. Sheath 41 extends throughout the length of the transparent glass tube 15 that is intermediate outlet member 25 and piston 32. Preferably, as shown in FIGS. 1–4, sheath 41 overlaps end fittings 16 and 17 to a substantial extent. Sheath 41 is formed of a material which inhibits the transmission of actinic light but which passes other light in the visible spectrum, so that limited inspection of the contents of dispenser 10, in chamber 38, can be made through the sheath. Scale 12 is also visible through sheath 41.

Preferably, the protective film sheath 41 is formed of a length of thin thermoplastic resin tubing. One suitable material for sheath 41 is tubing of polyvinyl chloride incorporating ultraviolet inhibitors having a thickness of 0.003 inch, usually of amber color. This tubing affords excellent protection against actinic light, somewhat better than most of the amber glass that has previously been used for syringes and like dispensers. The tubing is heated, as to a temperature of 350° F. for 2-3 seconds, to shrink it. On cooling, sheath 41 is mounted on the dispenser housing in an effective heat-shrink high-friction fit, tightly adherring to the outer surface of the syringe housing.

In the preferred construction shown in the drawings, sheath 41 includes two indented or perforated tear lines 42 and 43 which extend longitudinally of the sheath in spaced relation to each other. In diepsner 10, the tear lines 42 and 43 extend for the full length of sheath 41; if preferred, the tear lines may be limited to only a portion of the sheath length. The portion of sheath 41 intermediate tear lines 42 and 43 constitutes a removable tear strip 45. The spacing between tear lines 42 and 43 can be varied as desired. At one end of sheath 41 the tear strip 45 is extended in length, as compared with the adjacent portions of the sheath, affording a tab 44 to aid in removal of the tear strip.

A heat-shrink fit for sheath 41 is completely satisfactory in any application in which there is no need to retain any part of the sheath on the housing of dispenser 10 after the contents of the dispenser have been discharged. In some instances, however, it may be desirable to utilize the portion of sheath 41 outside tear strip 45 for the labelling purposes and to retain the label on the dispenser housing after the dispenser has been used. For such applications, the remaining portion of sheath 41, other than tear strip 45, may be adhesively bonded to the dispenser housing as a permanent label bearing printed or handwritten data 46 (FIGS. 1 and 4). A part of the label portion of sheath 41 may be printed or pigmented to afford a white or other light-colored opaque background and thus provide improved visibility for markings 46. This opaque portion of the sheath may be located immediately adjacent tear strip 45, as shown, or may be on the opposite side of the syringe sheath. In some instances, it may be desirable to apply printed or written legends 46A to tear strip 45 for supplemental use in record control and the like.

In the use of dispenser 10, chamber 38 is filled with the desired liquid medication or other material to be dispensed, through slit valve 35. The filling procedure is generally known in connection with the SOLOPAK syringes of MPL, Inc., and is described in the patents identified above, so that no specific description of the filling procedure is necessary here. After filling, the medication may be stored for a substantial period of time in dispenser 10, without danger of deterioration from actinic radiation, due to the protection afforded by sheath 41.

When it is desired to dispense the liquid from chamber 38, cap 23 is removed and plunger 14 is threaded into the receptacle 33 in piston 32. Tab 44 is pulled outwardly of syringe 10, in the manner illustrated in FIG. 2, pulling tear strip 45 from sheath 41 (see FIG. 4). If sheath 41 is not bonded to the housing of dispenser 10, other than by a heat-shrink fit, the entire sheath 41 can easily be stripped from the dispenser. On the other hand, if sheath 41 is being utilized as a label, as described above, the part of sheath 41 outside tear strip 45 remains in place on dispenser 10 as shown in FIGS. 3 and 4. In either event, the contents of syringe 10 are now clearly visible through its transparent housing, allowing full effective inspection of the syringe contents immediately prior to use.

For a hypodermic syringe, such as syringe 10, cap 22 is removed and is replaced by hypodermic needle 20 before discharge of the contents of the chamber 38 is commenced. For nebulizer injector syringes, a fill needle may be applied instead of hypodermic needle 20.

For oral dispensers, removal of cap 22 is sufficient, no needle being required.

To dispenser the contents of chamber 38, after installation of needle 20, plunger 14 is pushed into the housing of syringe dispenser 10 in the direction of arrow A (FIG. 3). The resulting forward movement of piston 32 applies fluid pressure to the valve-seal member 25, driving the seal member toward the outlet end of the syringe so that post 29 dislodges plug 27 to afford a fluid passage connecting chamber 38 with the syringe outlet 18 and needle 20. Thereafter, the continued movement of piston 32 axially of tube 15 discharges the contents of chamber 38 through outlet 18 and needle 20 as indicated in FIGS. 3 and 4.

The utilization of tear lines 42 and 43 to define a tear strip 45 in sheath 41 is not always necessary. If sheath 41 is inherently thin enough and weak enough so that it can be torn away from the syringe housing without any need for tools, the tear lines can be omitted. Even in these instances, however, it is usually desirable to provide a projecting tear tab, such as tab 44, to facilitate stripping away all or part of sheath 41 for inspection purposes prior to dispensation of the contents of syringe 10.

Although the invention has been described in connection with a particular commercial construction for the housing of syringe 10, it will be recognized that it can be applied equally well to virtually any syringe incorporating a clear, transparent housing. Thus, the invention is applicable to syringes in which the entire housing is formed of glass or to syringes that utilize a clear transparent plastic housing, provided the medication or other liquid is compatible with a housing of this kind. Moreover, the invention is not limited to use with any particular form of outlet seal, such as the valve-seal 25; these details of dispenser 10 have been illustrated only in order to afford a complete disclosure of a preferred construction for the invention.

We claim:

1. A syringe-type dispenser for storing and dispensing a liquid which is adversely affected by exposure to actinic light, comprising:
    a housing including a clear, transparent tube having an outlet at one end;
    outlet seal means, at the outlet end of the housing, including means for opening an outlet passage through the housing outlet;
    a piston in the other end of the tube, the outlet seal means and the piston conjointly defining a normally sealed chamber, within the tube, for storing the liquid to be dispensed, the piston being axially movable through the tube toward the outlet end of the housing to discharge the liquid through the outlet;
    and a thin, protective film sheath, covering and tightly fitting over the outside of the housing throughout the length of the tube between the seal means and the piston, the protective film sheath being formed of a material which inhibits the transmission of actinic light but passes other light in the visible spectrum to permit limited inspection of the dispenser contents, at least a part of the sheath being readily detachable to expose the contents of the dispenser for improved inspection directly through the housing.

2. A syringe-type dispenser according to claim 1 in which the protective film sheath is a length of thin thermoplastic tubing mounted on the housing in a heat-shrink high-friction fit.

3. A syringe-type dispenser, according to claim 2, in which the protective film sheath includes an extending tear tab to afford a means for removal of at least a part of the film from the dispenser housing to facilitate visual inspection of the dispenser contents prior to use.

4. A syringe-type dispenser according to claim 2, in which the protective film includes two weakened tear lines extending longitudinally of the sheath in spaced relation to each other to afford a removable tear strip in the sheath to facilitate visual inspection of the dispenser contents prior to use.

5. A syringe-type dispenser according to claim 4, in which a portion of the protective film sheath between the tear lines is longer than the adjacent portions of the sheath, affording an extending tear tab to aid in removal of the tear strip.

6. A syringe-type dispenser according to claim 4, in which the remaining portion of the protective sheath, other than the tear strip, is adhesively bonded to the dispenser housing as a permanent label thereon.

7. A syringe-type dispenser according to claim 1 in which at least a part of the label is substantially opaque, affording improved visibility for markings thereon.

* * * * *